US006912549B2

(12) United States Patent
Rotter et al.

(10) Patent No.: US 6,912,549 B2
(45) Date of Patent: Jun. 28, 2005

(54) SYSTEM FOR PROCESSING AND CONSOLIDATING RECORDS

(75) Inventors: Joann Molaro Rotter, Malvern, PA (US); Barbara Claire Brown, Malvern, PA (US)

(73) Assignee: Siemens Medical Solutions Health Services Corporation, Malvern, PA (US)

(*) Notice: Subject to any disclaimer, the term of this patent is extended or adjusted under 35 U.S.C. 154(b) by 540 days.

(21) Appl. No.: 09/993,041

(22) Filed: Nov. 6, 2001

(65) Prior Publication Data

US 2003/0046280 A1 Mar. 6, 2003

Related U.S. Application Data

(60) Provisional application No. 60/317,152, filed on Sep. 5, 2001.

(51) Int. Cl.[7] .............................................. G06F 17/30
(52) U.S. Cl. .............................. 707/200; 707/2; 707/6; 707/101
(58) Field of Search .............................. 707/1–6, 8–10, 707/100–102, 104.1, 200–203, 205, 206; 705/1–3; 709/200–203, 223, 224

(56) References Cited

U.S. PATENT DOCUMENTS

| | | | |
|---|---|---|---|
| 5,084,815 A | | 1/1992 | Mazzario .................... 395/800 |
| 5,497,486 A | * | 3/1996 | Stolfo et al. .................... 707/7 |
| 5,680,611 A | | 10/1997 | Rail et al. .................... 395/612 |
| 5,717,915 A | | 2/1998 | Stolfo et al. ................ 395/605 |
| 5,724,968 A | * | 3/1998 | Iliff ............................. 600/300 |
| 5,895,461 A | * | 4/1999 | De La Huerga et al. ........ 707/1 |
| 5,907,839 A | * | 5/1999 | Roth ............................. 707/5 |
| 5,970,497 A | | 10/1999 | Burrows .................... 707/102 |
| 6,061,503 A | | 5/2000 | Chamberlain .......... 395/200.47 |
| 6,168,568 B1 | * | 1/2001 | Gavriely .................... 600/529 |

(Continued)

FOREIGN PATENT DOCUMENTS

| | | |
|---|---|---|
| WO | WO 00/00915 | 1/2000 |
| WO | WO 01/02285 A3 | 3/2001 |
| WO | WO 01/22285 A2 | 3/2001 |

OTHER PUBLICATIONS

Daniel T. Heinze et al., "LifeCode: A Deployed Application for Automated Medical Coding", AI Magazine, Summer 2001, vol. 22 No. 2, ProQuest Computing, pp. 76–88.*

M. Garcia et al.: "Immunization Registers DeDuplication and Record Matching," Internet Publication—Scientific Technologies Corporation Online! 1999, XP002259647 www.immunizationregistries.com/white_papers/.

Carleton Corporation: "The Four Challenges of Customer–Centric Data Warehousing," Internet Publication Online! Nov. 1998 XP002259648 www.ctiforum.com/technology/crM/whitepaper/dwo.pdf>.

International Search Report.

*Primary Examiner*—Greta Robinson
*Assistant Examiner*—Harold E. Dodds, Jr.
(74) *Attorney, Agent, or Firm*—Alexander L. Burke

(57) ABSTRACT

A system prevents the creation of duplicate records and identifies, groups, and consolidates duplicate records and manages the associated workload. A method consolidates multiple records that are associated with a single entity and are stored in at least one record repository. The method involves identifying first and second records and applying record matching criteria to compare data element content of the first and second identified records to determine commonality data. The commonality data is indicative of a likelihood the first and second records are associated with a common entity. The first and second record content is merged into a composite record in response to the determined commonality data. One of the first and second records are selected as a surviving record based on earliest date of record creation or relative content of the first and second records.

28 Claims, 20 Drawing Sheets

U.S. PATENT DOCUMENTS

| | | | |
|---|---|---|---|
| 6,230,158 B1 | 5/2001 | Burrows | 707/102 |
| 6,295,541 B1 | 9/2001 | Bodnar et al. | 707/203 |
| 6,308,177 B1 * | 10/2001 | Israni et al. | 707/100 |
| 6,415,295 B1 * | 7/2002 | Feinberg | 707/104.1 |
| 6,480,859 B2 * | 11/2002 | Mittal et al. | 707/101 |
| 6,606,744 B1 * | 8/2003 | Mikurak | 717/174 |
| 6,666,874 B2 * | 12/2003 | Heitzmann et al. | 606/159 |

* cited by examiner

DUPLICATE ENROLLEE USER - MICROSOFT INTERNET EXPLORER

File  Edit  View  Favorites  Tools  Help

Back • → • ⊗ ☒ ⌂ | ⊙ Search ⭐ Favorites ⌚ History | ⌂ • ⊟ • ⊟ ⌨ •

Address ☐ SG=Authenticating+user&CR=WEB_PTMAIN.TPL&CRT=S&CW=INVISION&CPRFX=INVISION&...HTM&FETCHRETURN=Y&CPRFX=INVISION& ▼ ⇨ GO

USER: EAD002    ⊙ LOG OFF

○ DUPLICATE ENROLLEE WORK DUPLICATE SET DISPLAY

▽ WORKLIST SEARCH    RETURN    RESULTS: 25 OF 25 SETS

| SET NO | MATCH WEIGHT | NAME | SET LAST EAD UPDATE DATE | SET ENROLLEE CREATE DATE | SET STATUS | NO OF MEMBERS |
|---|---|---|---|---|---|---|
| 71 | 33.49 | JONES, MAC | 06/12/2001 | 02/12/2001 | IN PROGRESS | 2 |
| 43 | 34.01 | SMITH, REGAN | 05/15/2001 | 11/22/2000 | NO ACTIVITY | 2 |
| 45 | 37.57 | BROWN, JAMIE | 05/11/2001 | 01/29/2001 | NO ACTIVITY | 2 |
| 65 | 35.80 | JONES, JUDY | 05/03/2001 | 05/03/2001 | NO ACTIVITY | 2 |
| 75 | 84.58 | SMITH, SCOTT | 05/03/2001 | 05/03/2001 | NO ACTIVITY | 2 |
| 39 | 78.37 | BROWN, BETH | 04/30/2001 | 10/15/2000 | NO ACTIVITY | 2 |
| 37 | 28.49 | WHITE, OVF | 03/07/2001 | 10/30/2000 | NO ACTIVITY | 2 |
| 51 | 44.85 | SMITH, T | 03/01/2001 | 10/25/2000 | NO ACTIVITY | 2 |
| 13 | 63.23 | JONES, ROBERT | 01/22/2001 | 04/06/2000 | NO ACTIVITY | 2 |
| 49 | 35.55 | BROWN, TRICIA | 01/10/2001 | 10/24/2000 | NO ACTIVITY | 2 |
| 47 | 79.06 | WHITE, HUGH | 01/10/2001 | 09/13/2000 | NO ACTIVITY | 2 |

717 → (points to row 71)
719 → (points to row 45)

DONE                    LOCAL INTRANET

START | JOANN ROT... | X: DEPART... | SUPPLEME... | MISC SCREE... | TN3270... | DUPLICATE... | 1:35 PM

DUPLICATE ENROLLEE WORKSTATION

USER: EAD002 ☆ ⊖LOG OFF

- ▷ WORKLIST SEARCH
- SETS BY USER
- MEMBERS BY USER

COMPARE DUPLICATE ENROLLEES   SET NUMBER: 130   ACTIVITY

RETURN

| | | |
|---|---|---|
| NAME: | MARIA PATTERSON | MARIA PATTERSON |
| ENTERPRISE ID: | 000003979 | 000003949 |
| ADDRESS: | 33 SCHOOL LANE | 101 MAIN STREET |
| | WOODSTOWN, NJ 23838 | WOODSTOWN, NJ 23838 |
| HOME PHONE: | (093)409-3430 | (093)221-2121 |
| WORK PHONE: | | |
| MOTHER'S MAIDEN NAME: | | |
| SOC SEC NO: | 393-93-9393 | 393-39-9393 |
| SEX CODE: | F | F |
| RACE CODE: | CAU | CAU |
| MARITAL STATUS: | S | S |
| BIRTH DATE: | 10/31/1957 | 10/31/1957 |
| DEATH INDICATOR: | | |
| CREATE DATE: | 05/07/2001 | 05/03/2001 |
| LAST UPDATE DATE: | 08/02/2001 | 08/02/2001 |
| MERGE TARGET: | ● | ○ |

737 —

SELECT ONE OF THE FOLLOWING ACTIONS.
OPTIONS:     NOT DUPLICATE REASON: —— 734
730 —— MERGE ENROLLEES    [▼]  —— 736
732 —— COMPARE IDS          [MARK NOT DUPLICATE]

MEMBER STATUS: [▼]
[UPDATE STATUS]

DONE                          LOCAL INTRANET

FIG. 11

DUPLICATE ENROLLEE WORKSTATION | COMPARE IDENTIFIERS | USER: EAD002 ☆ ⊖LOG OFF

▷ WORKLIST SEARCH
SETS BY USER
MEMBERS BY USER

RETURN

SET NUMBER: 130

MARIA PATTERSON — 738

| IDENTIFIER | TYPE | ORGANIZATION | START DATE | END DATE |
|---|---|---|---|---|
| 104179 | MR | GBL | 05/07/2001 | |
| 1062850 | PN | GBL | 07/11/2001 | |
| 1062884 | PN | GBL | 07/10/2001 | |
| 1062868 | PN | GBL | 07/10/2001 | |
| 1061357 | PN | GBL | 05/18/2001 | |
| 1061142 | PN | GBL | 05/07/2001 | |
| 1061134 | PN | GBL | 05/07/2001 | |

MARIA PATTERSON — 739

| IDENTIFIER | TYPE | ORGANIZATION | START DATE | END DATE |
|---|---|---|---|---|
| 104173 | MR | GBL | 05/03/2001 | |
| 1063023 | PN | GBL | 07/12/2001 | |
| 1061423 | PN | GBL | 05/18/2001 | |
| 1061225 | PN | GBL | 05/14/2001 | |
| 1081068 | PN | GBL | 05/03/2001 | |

PAGE CREATED: THURSDAY, AUGUST 2, 2001 5:00 PM FOR: EAD002

TOP OF PAGE

DONE | LOCAL INTRANET

SYSTEM FOR PROCESSING AND CONSOLIDATING RECORDS

This is a non-provisional application of provisional application Ser. No. 60/317,152 by B. Brown et al. filed Sep. 5, 2001.

FIELD OF THE INVENTION

This invention concerns a system and user interface for processing and consolidating multiple records that are associated with a single entity and are stored in at least one record repository.

BACKGROUND OF THE INVENTION

Multiple records incorporating at least a portion of duplicated content are commonly generated in various organizations and enterprises. These duplicate records arise because of many reasons. They arise because of mergers of information databases resulting from alliances, acquisitions or mergers of companies, for example. They may also arise because of processing inefficiencies, data entry errors and mistakes as well as errors due to external factors and a lack of effective integrated record processing technology. Once created the redundant record information may result in further propagation of errors and mistakes and represents an additional storage and overhead burden unless the duplicate records are consolidated into a single record containing pertinent required information.

In the health care field, for example, health care providers and networks merge, form alliances and participate in community health information networks. As a result patient medical information from various disparate systems is stored in large databases or in one or more Electronic Master Patient Indexes (EMPI). If a patient has more than one record in an EMPI, it is possible that different patient clinical information, obtained during separate patient health care visits, is stored in different unrelated records. This results in a segmented patient record which may result in incorrect treatment being prescribed as well as drug interaction problems and may even result in the patient receiving no treatment and medication being delivered to the wrong person. Consequently, the existence of multiple segmented health care records for an individual patient exacerbates the likelihood of error in treatment of the patient and billing for services delivered to the patient. Further, the existence of multiple segmented health care records including duplicate information portions for an individual patient results in additional patient dissatisfaction since it is likely to lead to repetitive interrogation of the patient regarding health care history and circumstances.

A system according to invention principles addresses these problems.

SUMMARY OF INVENTION

A system minimizes creation of duplicate records and identifies, groups, and consolidates duplicate records and manages the associated workload. A method consolidates multiple records that are associated with a single entity and are stored in at least one record repository. The method involves identifying first and second records and applying record matching criteria to compare data element content of the first and second identified records to determine commonality data. The commonality data is indicative of a likelihood the first and second records are associated with a common entity. The first and second record content is merged into a composite record in response to the determined commonality data.

In a feature of the invention, one of the first and second records are selected as a surviving record based on earliest date of record creation or relative content of the first and second records.

BRIEF DESCRIPTION OF THE DRAWING

FIGS. 5–21 show display menus and results images for user interface functions of the sequential tasks performed in consolidating multiple records detailed in FIG. 4, according to invention principles.

DETAILED DESCRIPTION OF THE DRAWINGS

Figure 1:
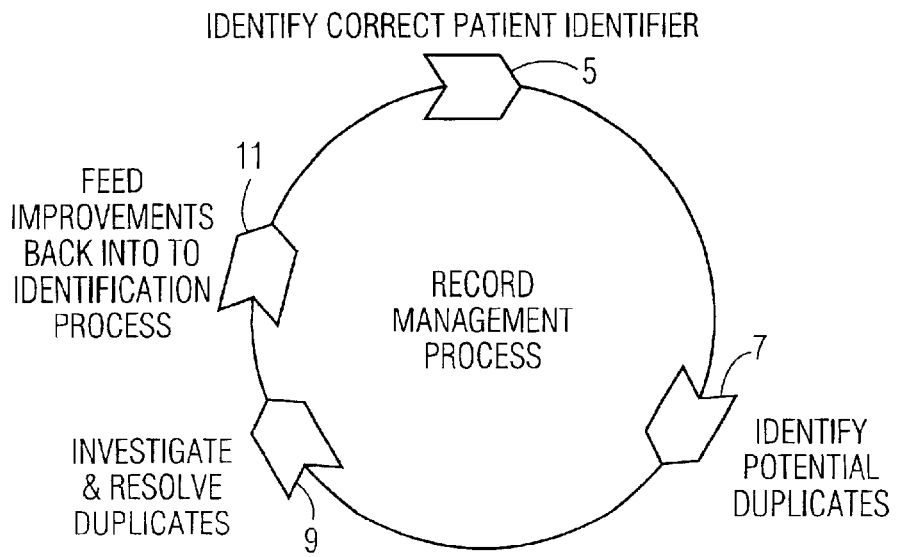
FIG. 1 shows an overview of an adaptive process for identifying and consolidating multiple records, according to invention principles.

FIG. 1 shows an overview of an adaptive process used by a system for identifying and consolidating multiple records. Although the system is described in the context of healthcare record processing, this is exemplary only. The system applies to any environment burdened by multiple records containing duplicative and redundant material. The term record is used herein to signify information or data that is material to a particular subject and that is preserved in non-volatile, permanent or tangible form such as in a computer file, disk, CDROM, DVD etc. or other electronic storage and is accessible by a computer or other electronic processing system. The term duplicate records is used herein to refer to records that contain one or more substantially equivalent information items and is not restricted to refer to records that contain significant or substantial mutually replicated content portions. Duplicate records is also used herein to refer to multiple (two or more) records containing duplicative and redundant material and is not restricted to meaning just two of such records. The system minimizes creation of duplicate records and identifies, groups, and consolidates duplicate records and manages the associated workload. It achieves this using sophisticated record element matching techniques employing probabilistic and deterministic logic in examining different data types and associated parameters in matching record elements. The matching techniques are used in assigning a weighting to potential duplicate records that is indicative of a degree of common information between the potential duplicate records. This weighting is indicative of the probability that the records are indeed duplicate records. The identified potential duplicate records are grouped into record sets for merging and other processing.

The system is implemented in a web based or intranet network environment as a process involving a sequence of tasks comprising a workflow that enables a user to identify and merge duplicate records. The process is performed either as a wholly automated process or as a process involving manual supervision of specific decisions that are predetermined as requiring such intervention. In the described health care environment, for example, clinical information in patient records may be designated as requiring user supervision prior to merging such information in a designated composite surviving record. In contrast, non-clinical information may be processed and merged into the composite record automatically. The items requiring such manual intervention are entirely user determinable.

Known systems available for use in the healthcare record processing field suffer from numerous deficiencies and do not offer the described system comprehensive capability for identifying, grouping, and resolving duplicate records as well as managing the associated workload. Specifically, known system deficiencies include unreliable duplicate record identification and inability to adaptively merge clinical and non-clinical record information. In addition, known systems do not offer the capability of automatically identifying and merging records including clinical or non-clinical data in an integrated and coherent operation. Further, known systems do not offer the capability of automated merging of record databases by applying the described record processing system.

FIG. 1 shows an overview of an adaptive process used by a system for identifying and consolidating multiple records and for automatically continuously improving its operation based on analysis of results. The adaptive process involves a one or more concurrently operating applications accessed in response to a single entry of user identification and password information via a displayed user authentication window. The process involves a sophisticated matching algorithm (SMA) using probabilistic logic. In particular, the matching algorithm is used in step 5 to identify correct existing identifiers and records for a patient, for example, at a patient admission, registration or other system entry point. This function is advantageously incorporated into a patient admission, patient record (e.g., clinical record) update or patient record interrogation process as well as into patient care scheduling and any other process that may lead to record alteration or creation. This enables the correct patient and any associated records to be identified at the points at which a patient encounters services of a healthcare enterprise. This also ensures patient laboratory test results or orders to a pharmacy, for example, are applied to the correct patient at any facility within a healthcare enterprise. Further, the matching function used in step 5 also advantageously includes an improved patient (and other information element) identifier search and matching capability. Thereby, the system minimizes the creation of duplicate records associated with a specific patient which typically occurs at areas where an initial patient contact is made with a healthcare enterprise.

Following identifying correct patients and existing records for the patient in step 5, the matching algorithm (SMA) is further applied in step 7 for identifying potential duplicate records associated with any alternative patients that were not identified in step 5. For this purpose, the matching algorithm uses probabilistic logic in searching for information elements that are common to both a record associated with an identified correct patient identifier and other records held by record repositories. The matching algorithm in step 7 assigns a weighting to potential duplicate records that is indicative both of the degree to which information is common to potential duplicate records and of the probability that the records are indeed duplicate records.

The identified potential duplicate records are grouped into record sets for merging and other processing. The identification of records with common information may also be used for specific organizational needs such as in performing case studies, statistical analysis or targeted marketing campaigns, for example. In alternative, non-healthcare embodiments, the functions of the FIG. 1 process are used in identifying multiple records associated with an entity other than a particular patient. Such an entity may comprise a company, an organization, a group of people, a manufactured item, a record, service or resource, for example.

The identified potential duplicate records which are grouped into record sets in step 7 are investigated and resolved in step 9 to avoid creation and perpetuation of segmented patient medical records. A surviving record is designated to hold composite information from the duplicate records and selected information elements are transferred to the surviving composite record based on predetermined rules. This may be done, either in a wholly automated fashion or subject to manual intervention. Further, in step 11 the results derived from investigating the identified potential duplicate records are analyzed and used to improve the patient identification and record identification functions of steps 5 and 7. Specifically, records falsely identified as being potential duplicate records that are in fact associated with different patients are indicated as being different records by data entry in a designated record table. This table is checked during subsequent record matching to prevent repetition of such a false positive match. Records may be falsely identified as being potential duplicate records for a variety of reasons. The records may be associated with individuals who are twins, or who are family members that have the same name except for an appended junior or senior name extension or because of a data entry error, for example.

The adaptive process and system of FIG. 1 comprehensively manages detection and resolution of duplicate records. For this purpose it employs probabilistic record matching to identify duplicate records for merging into a composite surviving record based on adaptive predetermined merging rules. The system of FIG. 1 also generates reports and tracking data supporting monitoring (e.g., via trend analysis) and improvement of the duplicate record management process. The monitoring capability enables identification of those healthcare system areas responsible for creating duplicate records and also allows review of workload, progress and productivity of personnel involved in resolving duplicate records. Thereby, under-performing areas of the healthcare and record management system are identified and improved. Further the monitoring capability may be used to view specific features of duplicate records within a record repository system. The different patient identifiers associated with a particular patient may be accessed from multiple different record repositories in an enterprise and viewed by a user in manually deciding which records are to be merged, for example. Similarly, other clinical and non-clinical data may be viewed in real time for one or more patients in supporting record merging decisions. Further, the duplicate record managing process of FIG. 1 may be incorporated as part of an Electronic Master Patient Index (EMPI) application to advantageously improve operation of the EMPI.

Figure 2:
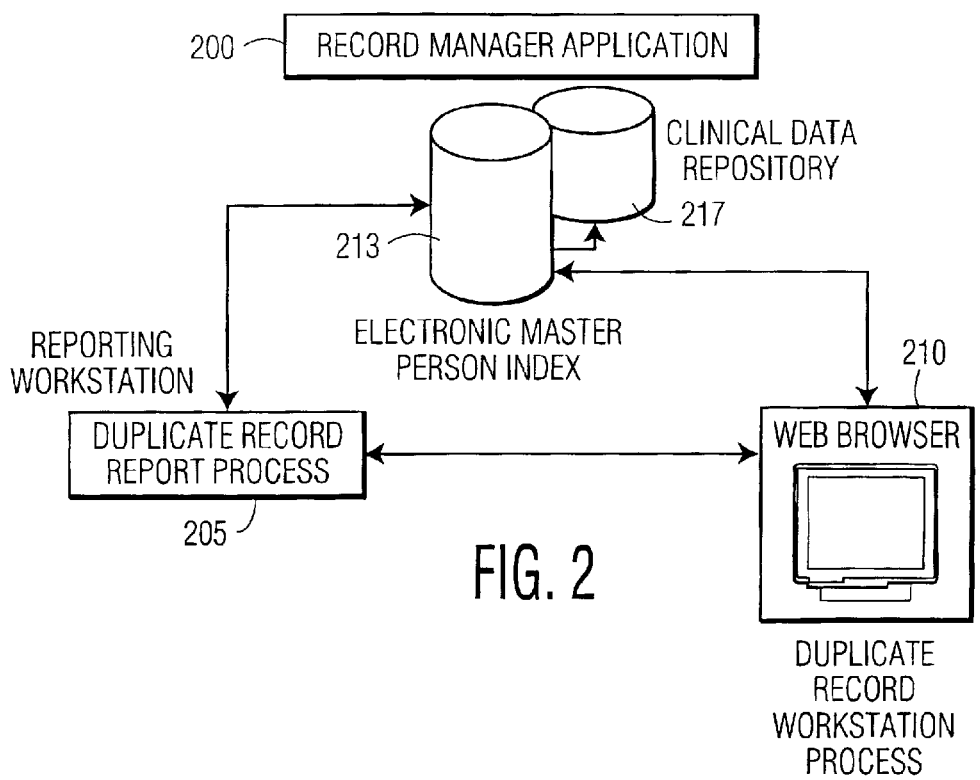
FIG. 2 shows a system including an application for preventing the creation of duplicate records and for consolidating multiple records that are associated with a single entity and managing the associated workload, according to invention principles.

FIG. 2 shows a system including an application for preventing the creation of duplicate records and for consolidating multiple records that are associated with a single entity (a patient in this example) and managing the associated workload. The system of FIG. 2 comprises application 200 operating on a server within a networked environment and communicating with a clinical data record repository 217 and Electronic Master Patient Index (EMPI) 213. Application 200 includes duplicate record management process 205 (described in step 7 of FIG. 1) and also includes results management process 210 (described in step 9 of FIG. 1) in processing results from process 205. In alternative embodiments, application 200 may reside on a PC, Personal Data Assistant (PDA) or another networked or mobile device. The duplicate record management process 205 identifies correct existing identifiers and records for a particular patient as well as potential duplicate records associated with any alternative patient identifiers of the particular patient using matching algorithms and probabilistic logic as described in connection with FIG. 1.

The identified potential duplicate records are grouped into record sets for merging into a composite surviving record and for data processing by process 210. Process 210 merges identified duplicate records based on predetermined user definable rules and stores non-clinical data (e.g. demographic data such as patient related administrative information including name, address, sex, age etc.) in a correctly identified patient record in EMPI 213. Process 210 also merges clinical data (e.g., laboratory results, test results, doctor diagnoses and notes, x-ray data etc.) stored in clinical data repository 217. The merge rules are determinable by a user to ensure data considered to be the most reliable is retained in a surviving record and inconsistent or redundant data is removed. The rules also allow all identification parameters such as patient identifiers to be retained irrespective of whether the identifiers are active or inactive. Process 210 further allows manual intervention in the merge process upon user command. For this purpose process 210 initiates generation of image menus supporting editing and amendment of patient identifier and other codes and data in the surviving composite record. Alternatively, process 210 automatically merges record data based on predetermined rules.

Processes 205 and 210 generate reports and tracking and process improvement data (e.g., data for eliminating false duplicate record identification data) supporting monitoring and improvement of the duplicate record management process. For this purpose processes 205 and 210 also generate data and statistics for analyzing and categorizing progress made in resolving identified duplicate records. Process 210 also provides basic administrative and task assignment and scheduling functions such as assigning potential duplicate record sets to users to be resolved. Process 210 further supports viewing and selecting potential duplicate record sets as well as viewing and selecting individual records and data elements in a duplicate record set. In addition process 210 enables comparison of duplicate record patient identifiers and clinical data as well as non-clinical data to facilitate user determination that the records are truly duplicates. This is done by generating different selectable user interface menus and images, such as a side by side record comparison image, formatted to assist data element comparison.

Figure 3:
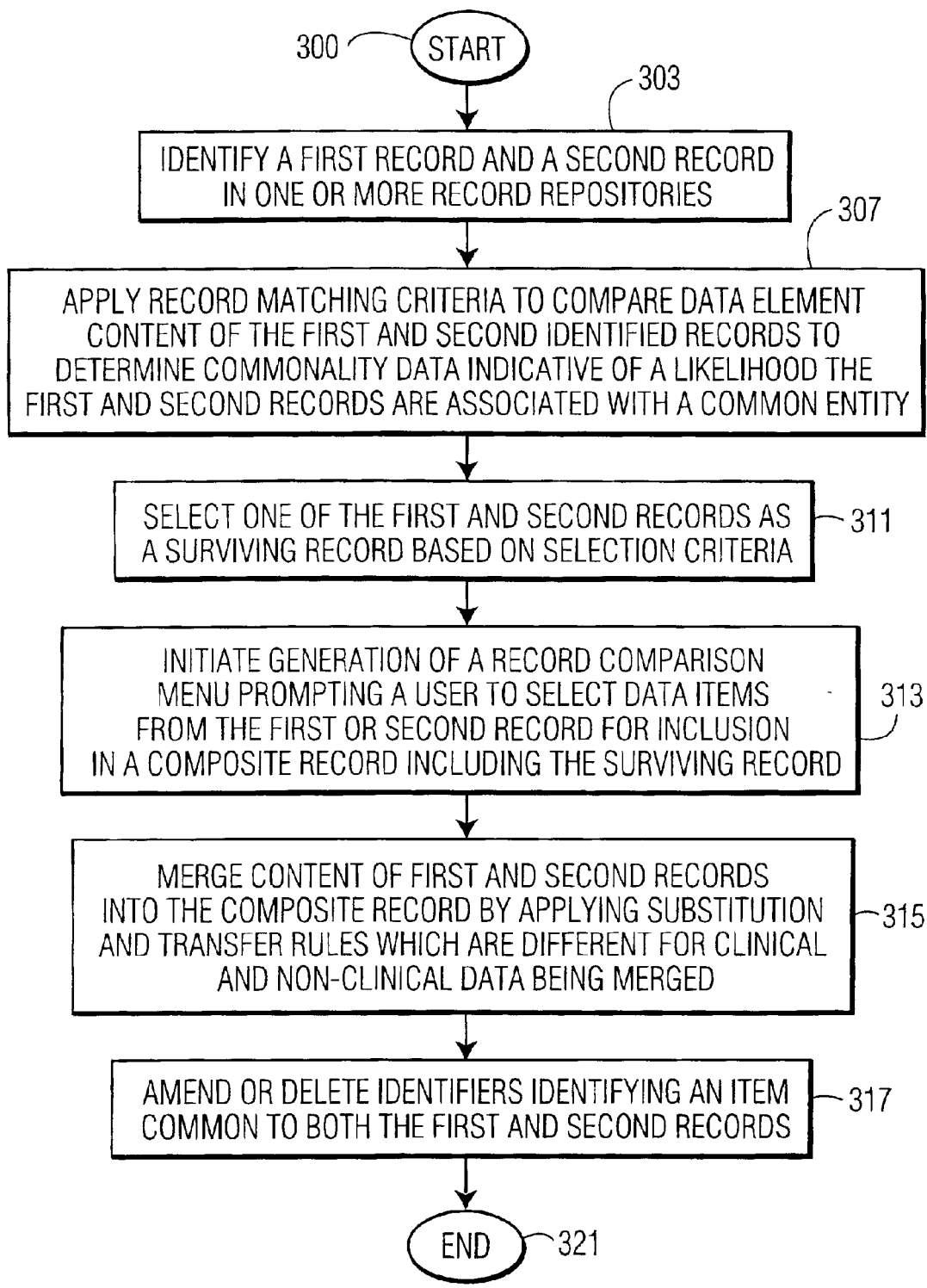
FIG. 3 shows a flowchart of a process for consolidating multiple records that are associated with a single entity and are stored in at least one record repository, according to invention principles.

FIG. 3 shows a flowchart of a process employed by application 200 (FIG. 2) for consolidating multiple records that are associated with a single entity and are stored in at least one record repository. Application 200 in step 303 of FIG. 3, after the start at step 300, identifies a correct existing first record (e.g. in EMPI 213 of FIG. 2) for a particular patient. Application 200 also identifies a second record associated with an alternative second patient identifier of the particular patient. This is done using matching algorithms and probabilistic logic as previously described in connection with FIG. 1. In step 307, application 200 applies record matching criteria to compare data element content of the first and second identified records to determine commonality data indicative of a likelihood the first and second records are associated with a common entity (here the particular patient). Specifically, application 200 parses the first and second records and uses probabilistic matching logic to identify presence in the records of multiple predetermined record fields. The probabilistic matching logic uses multiple fields to perform a search and declares a match based on partial data in fields or based on transposed data in fields. Thereby, the probabilistic matching function is able to declare a match even when an exact item match is not present. This improves the effectiveness of the search system. The matching function also assigns weights that indicate the probability of a match and employs frequency analysis to assign a higher weight to less common values. Based on the probabilistic matching results, application 200 generates commonality data comprising a measure quantifying detected occurrence of predetermined record items in both the first and second records.

In step 311, application 200 marks either the first or second record to be a surviving record based on the greatest degree of commonality of data. Alternatively, in another embodiment a user selects a surviving record based on relative content of the first and second records or on other user selectable criteria. In step 313, application 200 initiates generation of a record comparison menu prompting a user to select data items from the first or second record for inclusion in a composite record containing the surviving record. Multiple different record comparison menus may be generated as required by a user to facilitate user comparison and selection of data items (e.g., a side by side menu comparing a first data item of the first record and a corresponding second data item of the second record). The generated menu also supports user amendment or deletion of patient identifiers and other identifier codes.

Application 200 in step 315 merges content of the first and second records into the composite record by applying substitution and transfer rules. Further, application 200 applies different rules in merging clinical data than in merging non-clinical data of the first and second records. Specifically, application 200 automatically incorporates clinical data of both the first and second records in the composite record unless a predetermined condition is satisfied indicating that the clinical data is to be merged subject to manual involvement. In the exemplary embodiment, the predetermined condition is satisfied if either, the patient concerned is on a particular physician patient list, or the clinical data of the second record duplicates the clinical data of the first record. Alternatively, if manual involvement is triggered, the clinical record data of the first and second records is displayed in a menu giving a side by side comparison of corresponding record elements. This allows a user to indicate which elements from either record are to be included in the composite record. The type of clinical data merged in step 315 includes, for example, electrocardiograph (ECG) or electro-encepholograph (EEG) data, x-ray data, laboratory test result data, physical characteristic data, previous diagnosis data, allergy data, ventilation data, blood oxygen or pressure data, infusion pump data and pulse data.

In addition, application 200 applies a variety of other user selectable rules in automatically including an individual record element of the first or second record in the composite record. Such rules include, for example, (a) including only a particular element of the first record in the composite record, (b) including only a particular element of the second record in the composite record, (c) including a first record particular element in the composite record if it is present, otherwise include the particular element from the second record, and (d) including a second record particular element in the composite record if it is present, otherwise include the first record particular element. Further, such rules may be selected by a user to apply to particular data items or sections of the first and second records or to the entire records.

Application 200 automatically substitutes particular non-clinical record elements of the chosen surviving record for corresponding elements of the non-chosen record for inclusion in the composite record. Such particular non-clinical elements include, for example, patient address information, patient name, patient physical characteristics or other patient non-clinical data. Similarly, the transfer rules applied in step 317 also automatically transfer particular record elements of the non-chosen record into the surviving record to form the composite record. Such particular record elements include a user identifier as well as record entries concerning medical services delivered to the patient. The transfer and substitution rules applied in the described embodiment in connection with step 315 comprise an automatic process with predetermined manual intervention upon the detection of particular record conditions. This is exemplary only. In alternative embodiments the process may use different rules and may be wholly automatic or entirely manual. The degree of manual intervention is user determinable. In step 317 in response to commands received via a generated menu, application 200 edits the identifiers in the composite surviving record. It does this by deleting a redundant identifier identifying an item common to both the first and second record from the composite record, or by amending an identifier identifying an item common to both the first and second record in the composite record. A deleted or amended identifier may identify a specific patient, a patient record, an element of a patient record and particular patient clinical data, for example. The process of FIG. 3 terminates at step 321.

Figure 4:
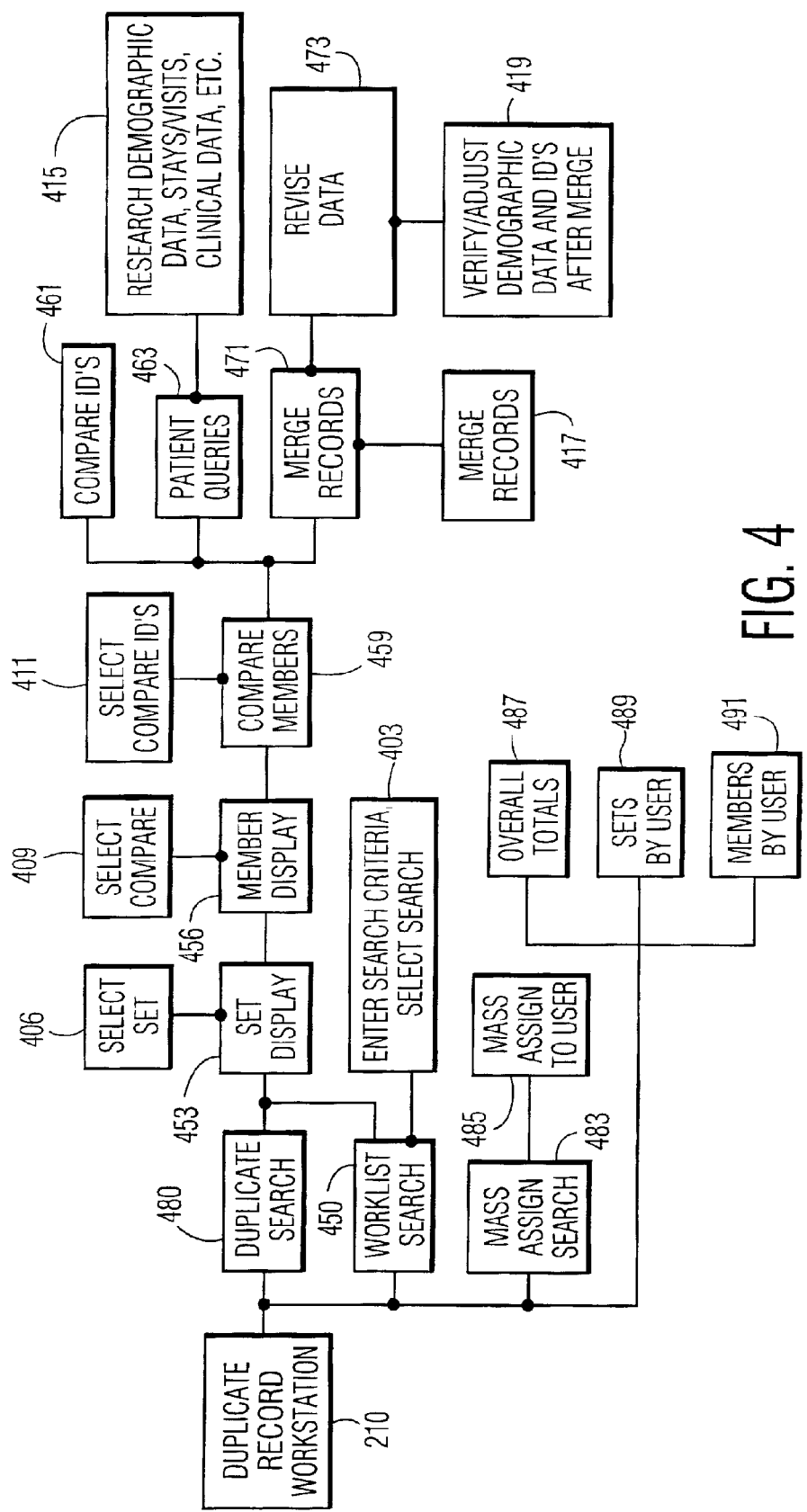
FIG. 4 shows a process detailing sequential tasks performed in consolidating multiple records that are associated with a single entity and are stored in at least one record repository, according to invention principles.
Figure 6:

FIG. 4 shows a process detailing sequential tasks (a workflow) performed in consolidating multiple records that are associated with a single entity and are stored in at least one record repository. The sequential tasks are used in resolving and merging duplicate records identified as described in connection with FIG. 1. An administrator also uses the workflow to evaluate, and monitor the workload of duplicate records assigned to particular individuals and is able to assign (and re-assign) sets of duplicate records to be resolved to specific personnel. FIGS. 5–21 show display menus and results images for user interface functions of the sequential tasks performed in consolidating multiple records detailed in FIG. 4.

An administrator is able to assign duplicate records in bulk to be resolved by multiple different users. In order to assign duplicate records to be resolved, an administrator performs a search on the previously identified duplicate record sets in step 483 of FIG. 4 using the user interface menu of FIG. 5. The search is performed based on criteria such as last activity date (selected using icon 501 of FIG. 5 and calendar windows of FIG. 5), creation date (selected using icon 503 and calendar windows of FIG. 5), or ease of resolution. Record sets involving more than two records e.g., associated with two or more different alternative patient identifiers are deemed more difficult to resolve than dual record sets, for example. Record pairs, triples etc. (reflecting resolution complexity) are selected for search via icon 504 and records assigned to specific users are selected for search via icon 505 of FIG. 5. The results of the search in the form of identified duplicate records for resolution are indicated in the interface menu of FIG. 6 which also allows an administrator to assign the indicated records to one or more users for resolution via icons such as icon 510, for example. An administrator is further able to refine workloads by performing a search and re-assignment of lists of prior assigned work in step 450 based on criteria entered in step 403 of FIG. 4, for example.

Figure 7:
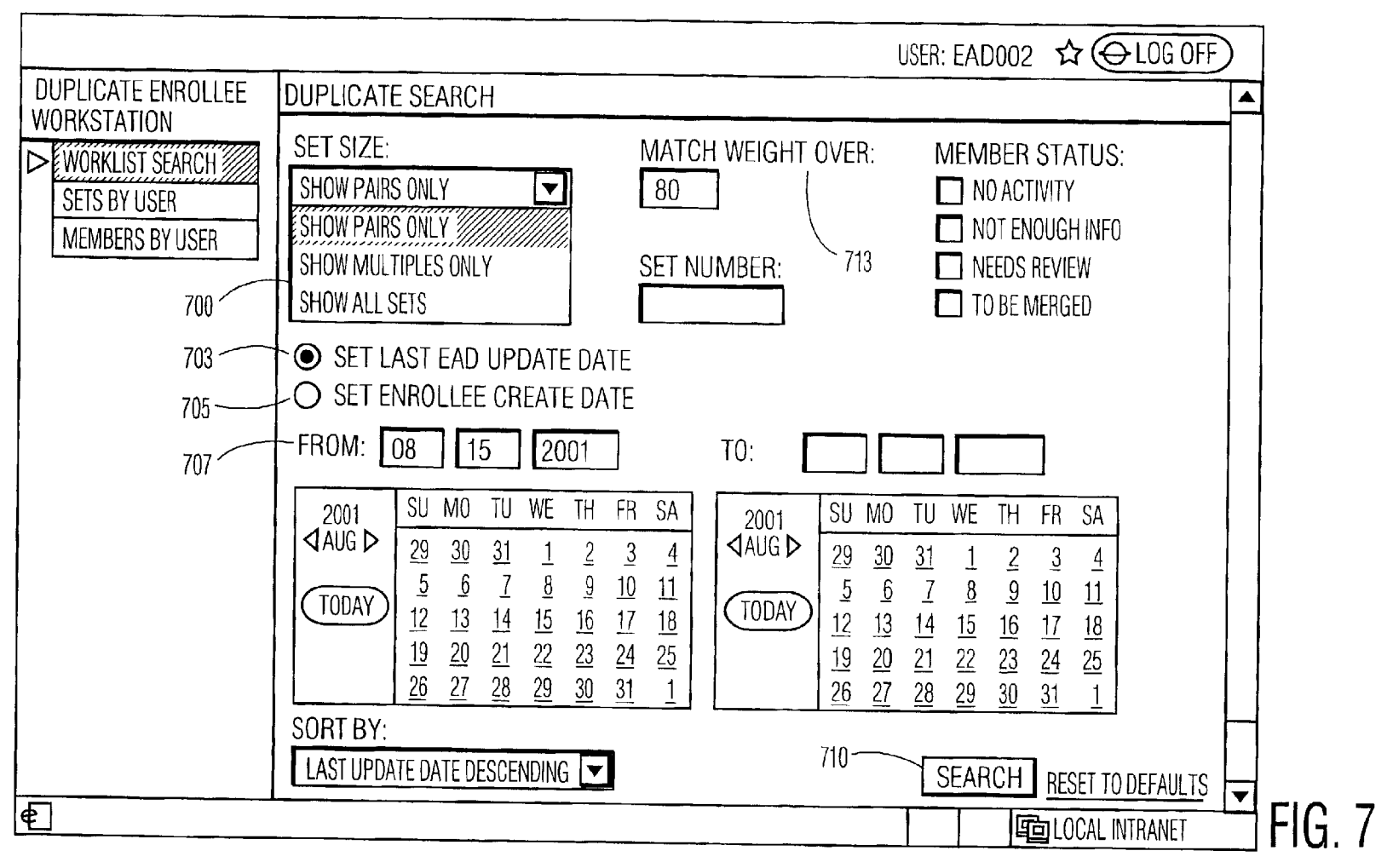

A user accesses assigned sets of duplicate records via workstation 210 and is able to perform additional searching, filtering and sorting of assigned duplicate record sets in step 450 using a menu as exemplified in FIG. 7 in response to a search initiation command via icon 710. A user search, like an administrator search, is performed based on criteria such as last activity date (selected using icons 703, 707 and calendar windows of FIG. 7), creation date (selected using icons 705, 707 and calendar windows of FIG. 7), or type of record set (e.g. dual, triple etc., record set selected via window 700). A user is also able to select as a threshold search criteria the degree of commonality between records in a duplicate record set via icon 713 (matching weight selection). The record sets identified by the search of step 450 are displayed in step 453 in a search results window as exemplified in FIG. 8. Individual record items 717, 719 of FIG. 8 show commonality data, patient name, record update date, record creation date, status and number of records in a set. Upon user selection of an individual record set in the menu of FIG. 8 in step 406, the individual records (e.g., records 723 and 725) comprising a set are displayed in step 456 (FIG. 4) in a window exemplified in FIG. 9.

Figure 9:
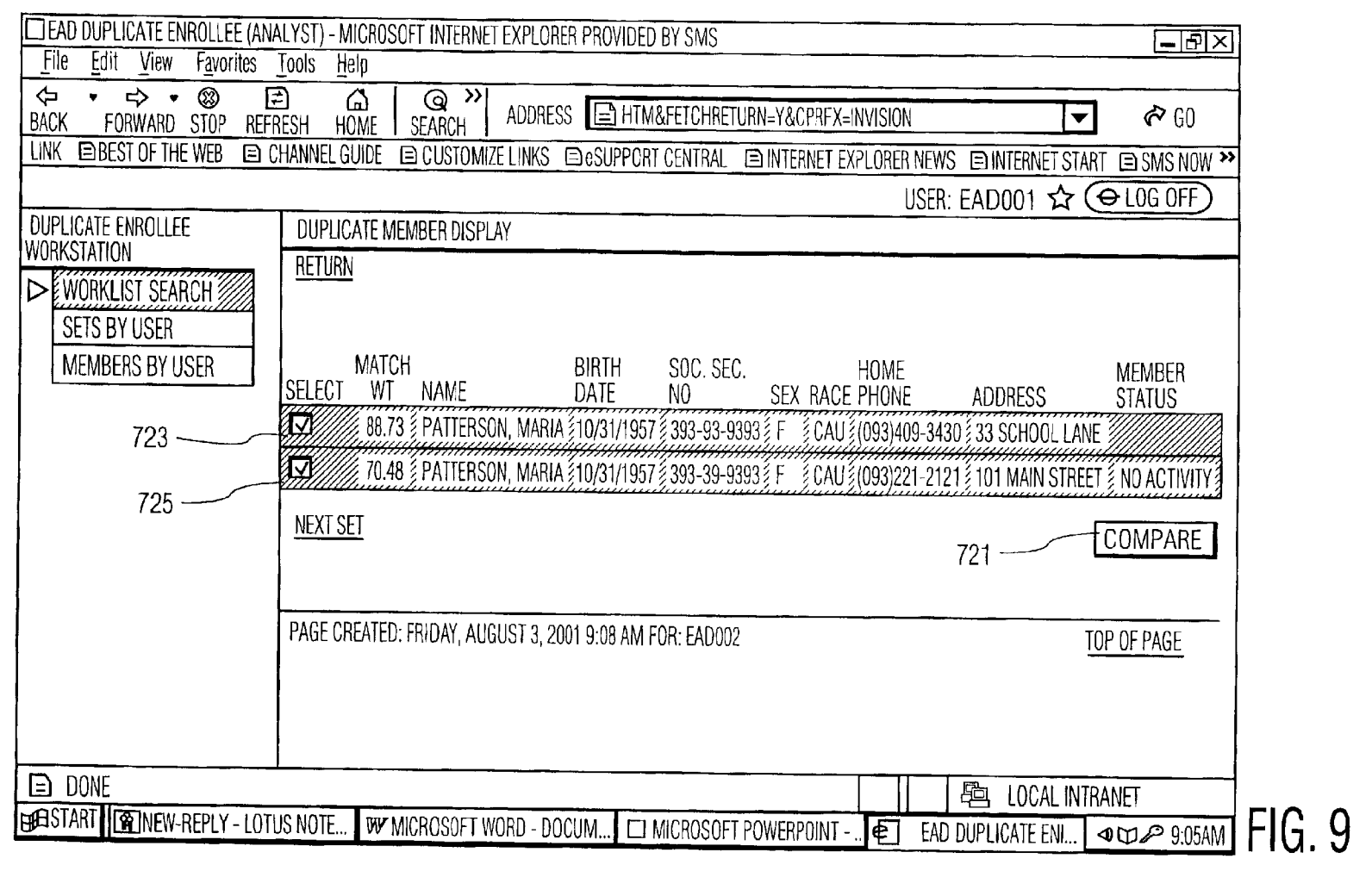

In response to user selection of the compare function in step 409 via icon 721 of FIG. 9 the individual member records comprising the set are presented in step 459 (FIG. 4) in a side by side comparison menu as exemplified in FIG. 10. The displayed comparison menu of FIG. 10 advantageously highlights record element differences between the records comprising a duplicate record set in order to facilitate manual resolution by a user. A user also advantageously employs the comparison menu of FIG. 10 to indicate records in a set are false positives via item 736 and are not duplicates. This occurs in the case that the records are associated with different individuals such as twins, or family members with the same name differentiated using Junior/Senior, for example. A user also employs the FIG. 10 comparison menu to assign a user determinable status to a record set using item 734. Such a status may indicate "Not enough information", "Needs review by a supervisor", or "To be merged", for example, and is definable by a user. Such a status indication identifies a record set as in progress until further action is performed. Further, a user is able to use the menu of FIG. 10 to initiate a comparison of identifier codes found in the records of a duplicate record set and is also able to initiate merger of duplicate record contents. This is achieved via use of FIG. 10 hyperlink items 732 and 730 respectively.

In response to user selection in step 411 (FIG. 4) of FIG. 10 hyperlink item 732, the duplicate records being compared in FIG. 10 are parsed and examined in step 461 (FIG. 4) to locate their various different identifier codes. The located identifier codes comprising Medical Record identifiers, Patient identifiers or other identifiers, for example, are displayed in step 461 in a side by side comparison menu exemplified in FIG. 11. The identifiers of the two records are compared side by side in items 738 and 739 of FIG. 11 and reveal a history of visits and other encounters that the patient concerned has had with a medical enterprise.

Figure 12:
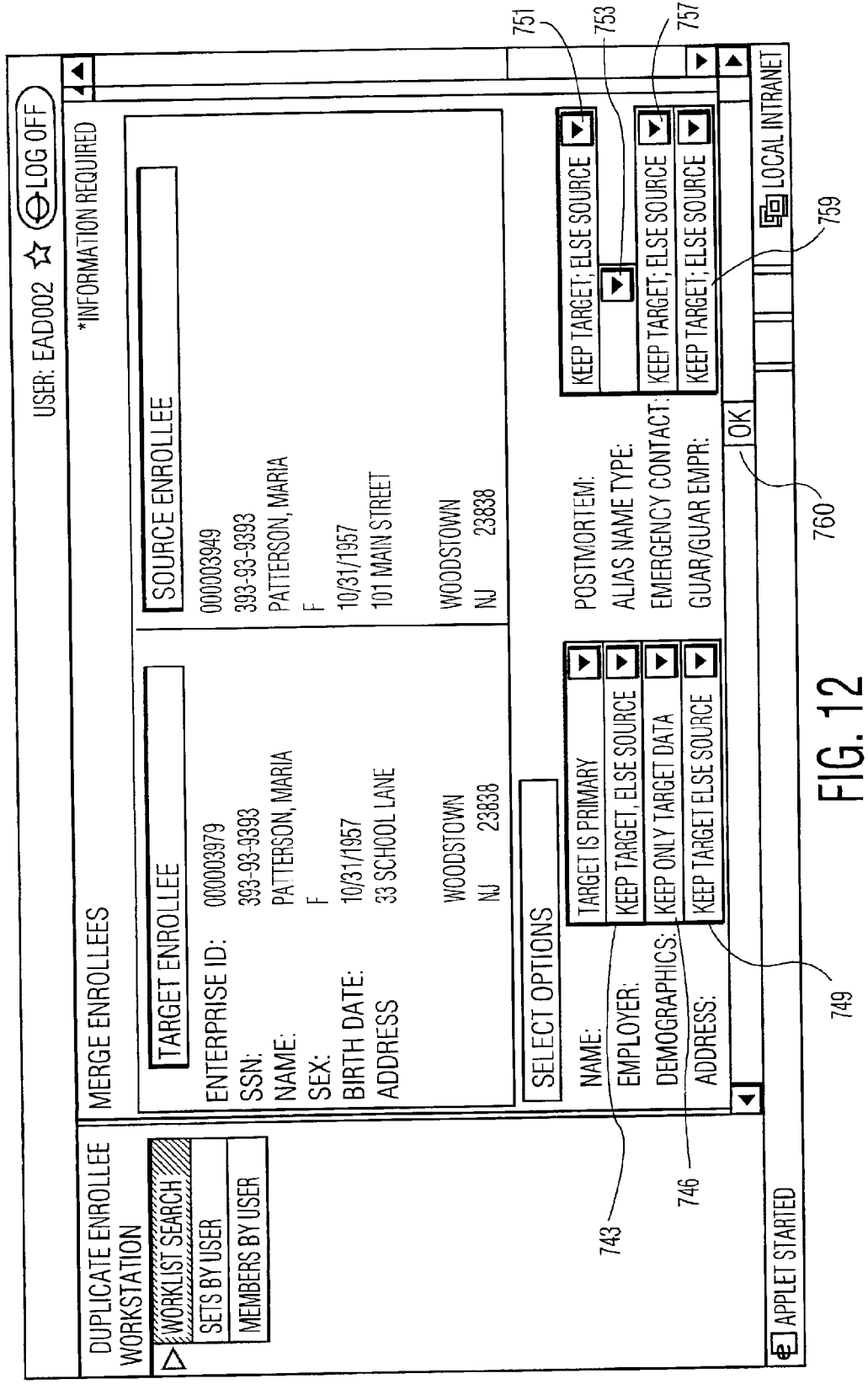

Upon determination that records are duplicates, a user initiates a merger process in step 471 (FIG. 4) of FIG. 10 via selection of hyperlink item 730 (Merge Enrollees). In response to selection of icon 730, a user interface window supporting the duplicate record merger function as exemplified in FIG. 12 is displayed in step 417 of FIG. 4. The system automatically designates the record of the duplicate record set with the highest degree of commonality data as a surviving (target) record to be the basis of the resultant merged composite record. However, a record with the earlier medical record number (or another criteria) may also be chosen as the target surviving record or a user may override this designation and select a particular record of the duplicate record set to be the surviving record via item 737 (FIG. 10). The remaining (source) record that is not selected to be the target record is retired upon completion of the merger. A user may also apply predetermined rules to designate from which record (target or source record) particular record information elements are to be incorporated into the target surviving record via items 743 to 759. The target and source record identifiers and clinical information are also incorporated in the resultant surviving composite record without editing in this exemplary embodiment.

The data automatically transferred from the source to the target surviving record includes, for example, User identifiers, Event tracking entries (Events are inpatient stays, visits and other encounters) and Insurance Plan related entries. Certain other categories of data are selectable from either the target or source record for inclusion in the surviving record based on user selectable predetermined rules. These categories of data include, for example, Demographic data (i.e., age, sex, height, weight, eye color etc.), Address data, Postmortem related data, Employer data, Guarantor and guarantor employer data, Emergency contact, Name, Organization class, User data and Insurance Policy identification data. The user selectable predetermined rules (selected via items 743–759 of FIG. 12), employed in processing these categories of data include, for example, (i) retaining a particular element of the target record in the surviving record, and (ii) retaining a particular element of the source record in the surviving record. Other rules employed in processing these categories of data include, for example, (iii) retaining a target record particular element in the surviving record if it is present, otherwise retaining the particular element from the source record, and (iv) retaining a source record particular element in the surviving record if it is present, otherwise retaining the target record particular element.

A user also selects rules for merging source record and target record clinical information (e.g., clinical results and observations such as lab/radiology results, links to documents, etc.) into a surviving composite record. These rules are similarly selected from predetermined items such as items 743–759 of FIG. 12 (but are not shown in FIG. 12 to preserve drawing clarity). The selectable predetermined clinical information merge rules enable particular preferred clinical information elements to be selected from either the source or target records. One rule, for example, initiates automatically merging clinical results unless a patient associated with the source record is currently included in a clinician's active patient list. Another rule initiates automatically merging clinical results unless the target and source records contain result information that is be considered to be redundant and duplicative. Such redundant result information is advantageously identified based on multiple factors including the same date and time, accession number and origin code. If a user has enabled these two rules, an error message is provided to the user upon on of the rule exception conditions being satisfied and manual intervention in the clinical information merge process is invoked. Whereupon a user employs Move, Copy, and Delete functions to manually manipulate and merge the clinical information from the source and target records into the surviving composite record. In another option, an error message may also be selected for generation to invoke manual intervention when clinical information is detected in the source record. A user selects icon 760 of FIG. 12 to initiate automatic merger of source and target records. This is done upon completion of any manual merger process.

In another embodiment, a user may also elect fully automatic merger via an icon (not shown) in the FIG. 12 window (involving no manual intervention) of either or both clinical information or non-clinical information from source and target records into the surviving composite record. Further in alternative embodiments manual intervention of either clinical or non-clinical information (or particular selected elements thereof) may be mandatory or only triggered upon particular conditions as exemplified in the previous description. Such automatic merger of source and target record information is performed based on predetermined rules also exemplified in the previous description.

Following completion of the merger of source and target record information into a composite surviving record, the composite record information is examined and edited by a user in steps 415 and 419 of FIG. 4. In particular, a user in step 415 of FIG. 4 is able to choose to view non-clinical or identifier data in the resultant merged composite record through generation of an interface window exemplified in FIG. 13. Thereby, a user in step 419 selects to view and revise non-clinical or identifier data via selection of icons 770 and 771 respectively together with selection of icon 773 in the user interface window of FIG. 13. The FIG. 13 window also displays the patient name 765 and social security number 767 for the patient associated with the composite record. The display window 775 of FIG. 14 permits user review or editing of non-clinical information and is displayed in response to user selection of items 770 and 773 in FIG. 13. Information is updated via window 775 (FIG. 14) and submitted in step 473 of FIG. 4 in response to user selection of icon 780 of FIG. 14. The display window 778 of FIG. 15 permits user review or editing of identifier information and is displayed in response to user selection of items 771 and 773 in FIG. 13. Information is updated via window 778 (FIG. 15) and submitted in step 473 of FIG. 4 in response to user selection of icon 781 of FIG. 15.

Figure 16:
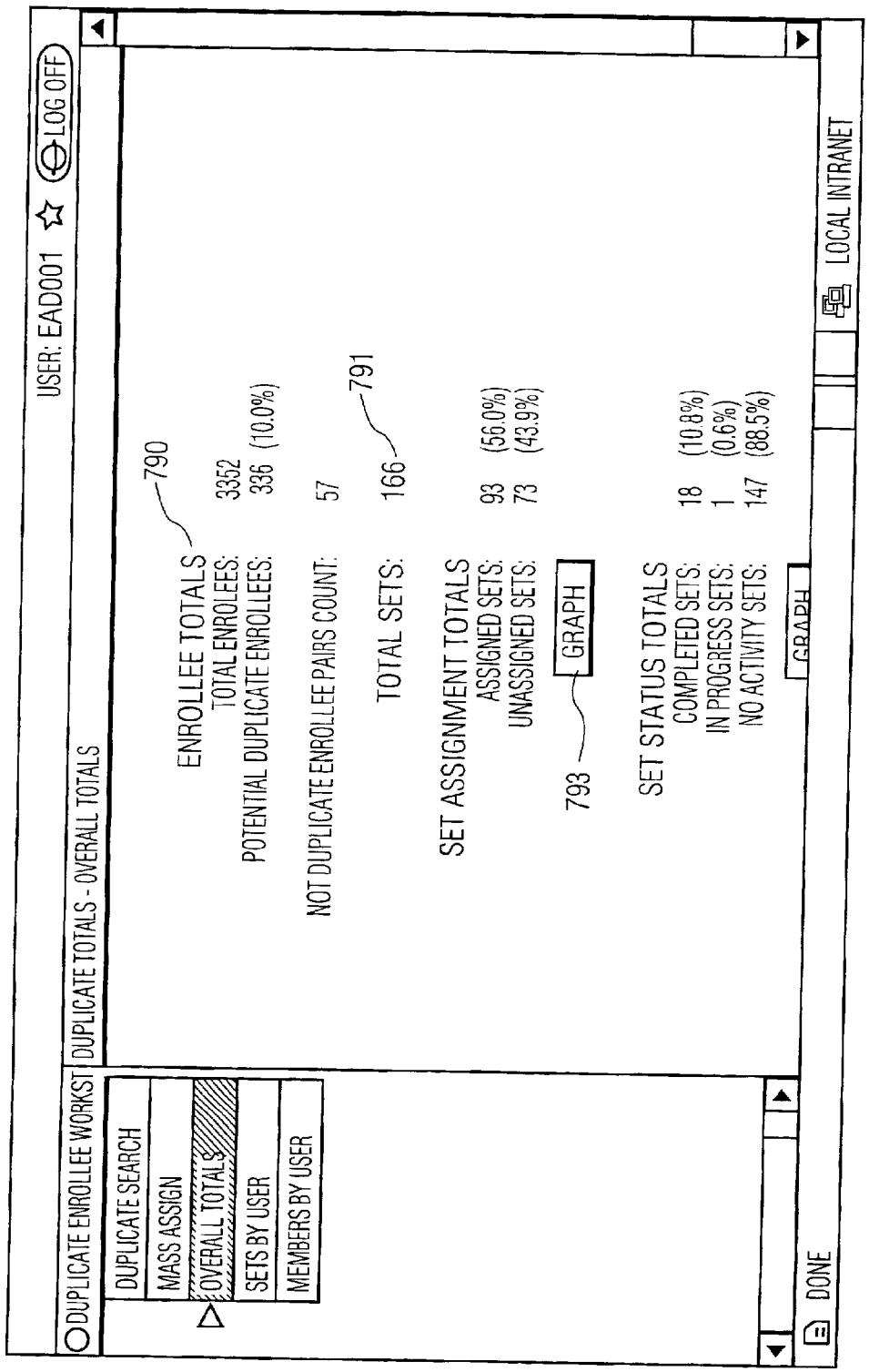
Figure 17:
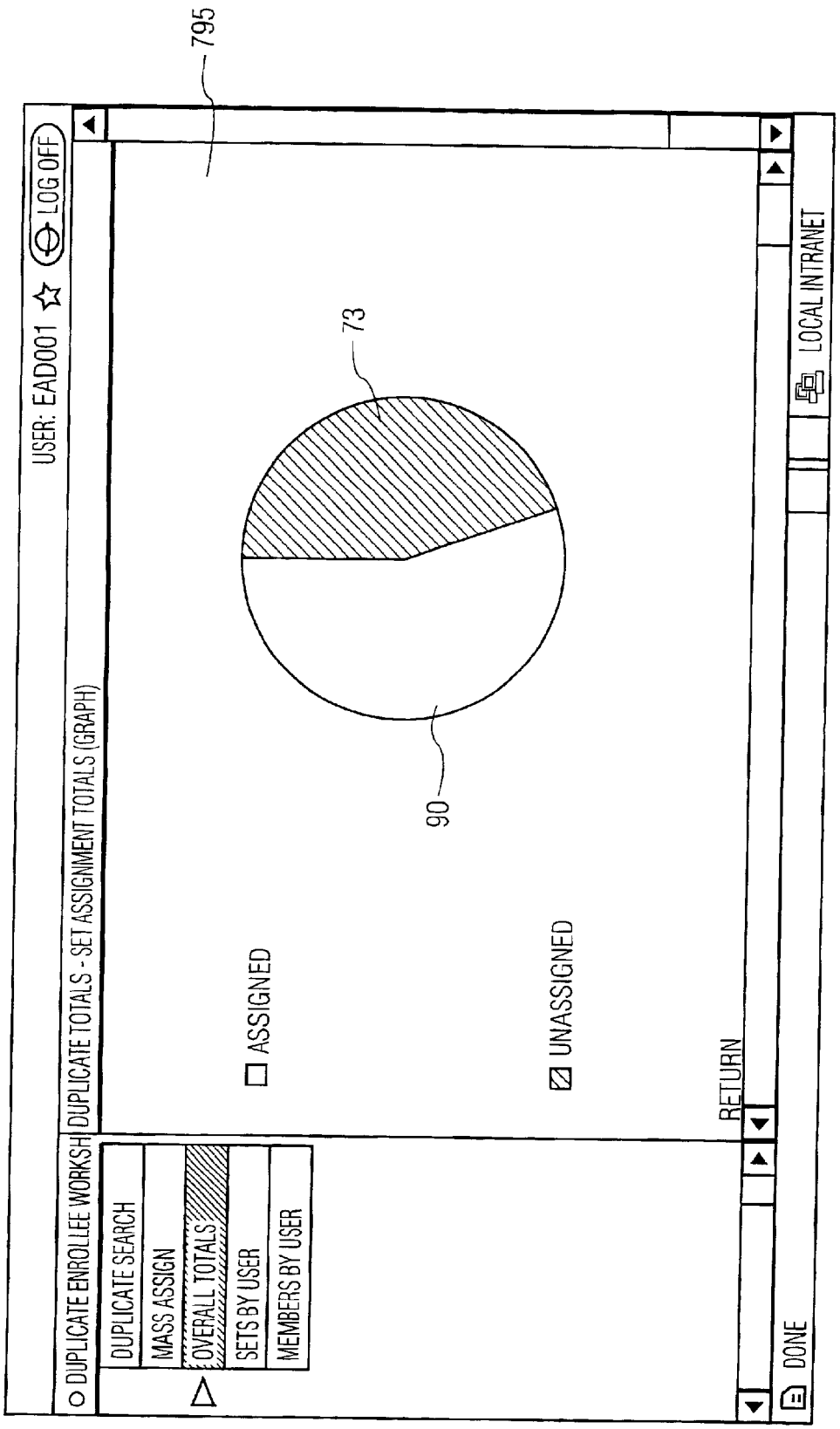

An administrator monitors operation and progress in resolving identified duplicate records through the generation and display of statistics objectively quantifying (by user and groups of users) resolution completion data, outstanding workload, other status indicators and the speed and complexity of the resolution operation. In step 487 of FIG. 4 a user interface window shown in FIG. 16 is generated in response to administrator command revealing the total records and potential number of patients associated with duplicate records (item 790). The window of FIG. 16 also indicates the total number of unresolved duplicate record sets to be processed (item 791) and the number of record sets assigned to users for resolution as well as the number of unassigned record sets and other statistics. Further, statistics given in FIG. 16 may be selected for presentation in graphical form. As an example, in response to user selection of graph icon 793 the number of record sets assigned to users for resolution as well as the number of unassigned record sets are graphically presented as items 73 and 90 of FIG. 17 window 795.

Figure 18:
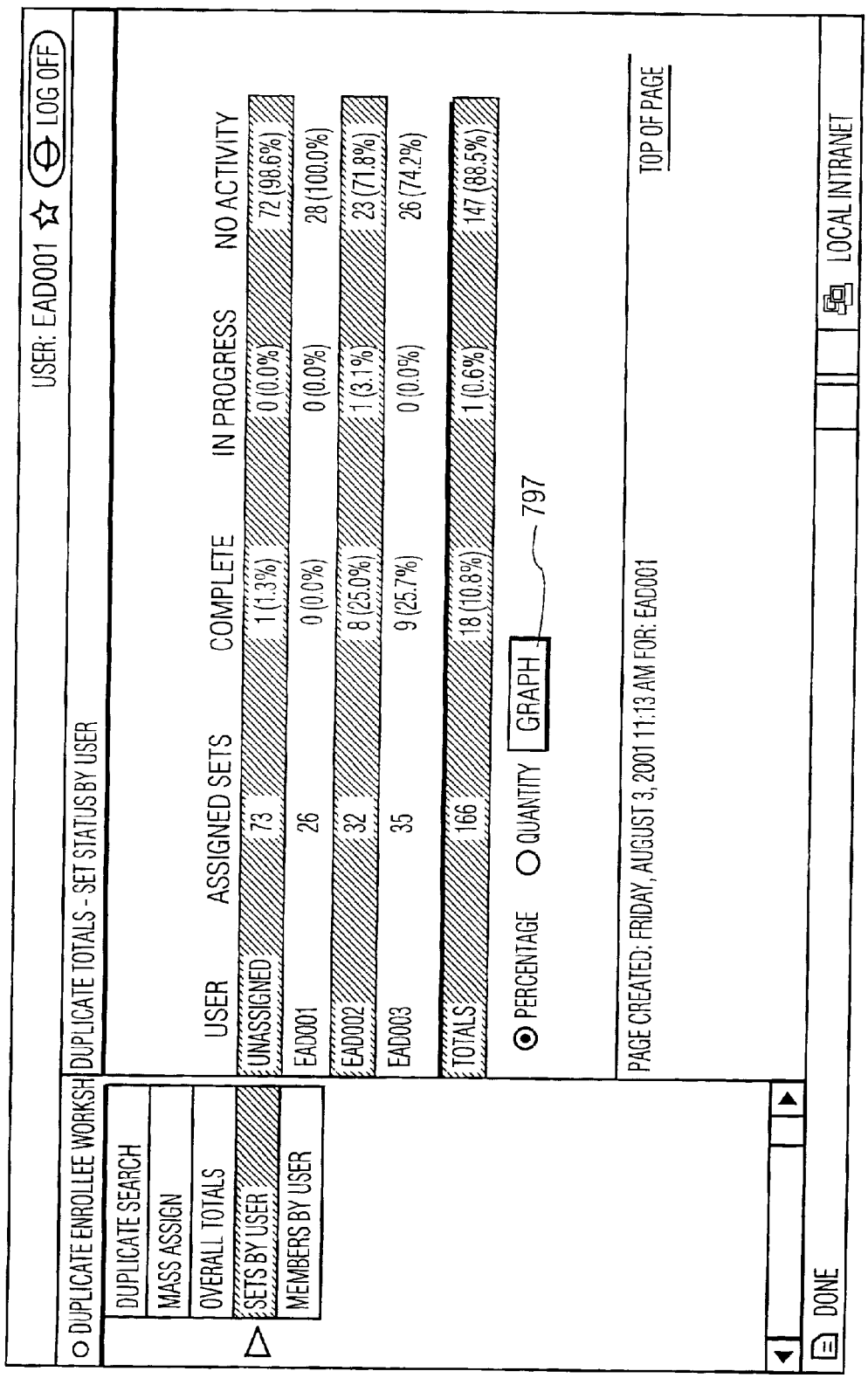
Figure 19:
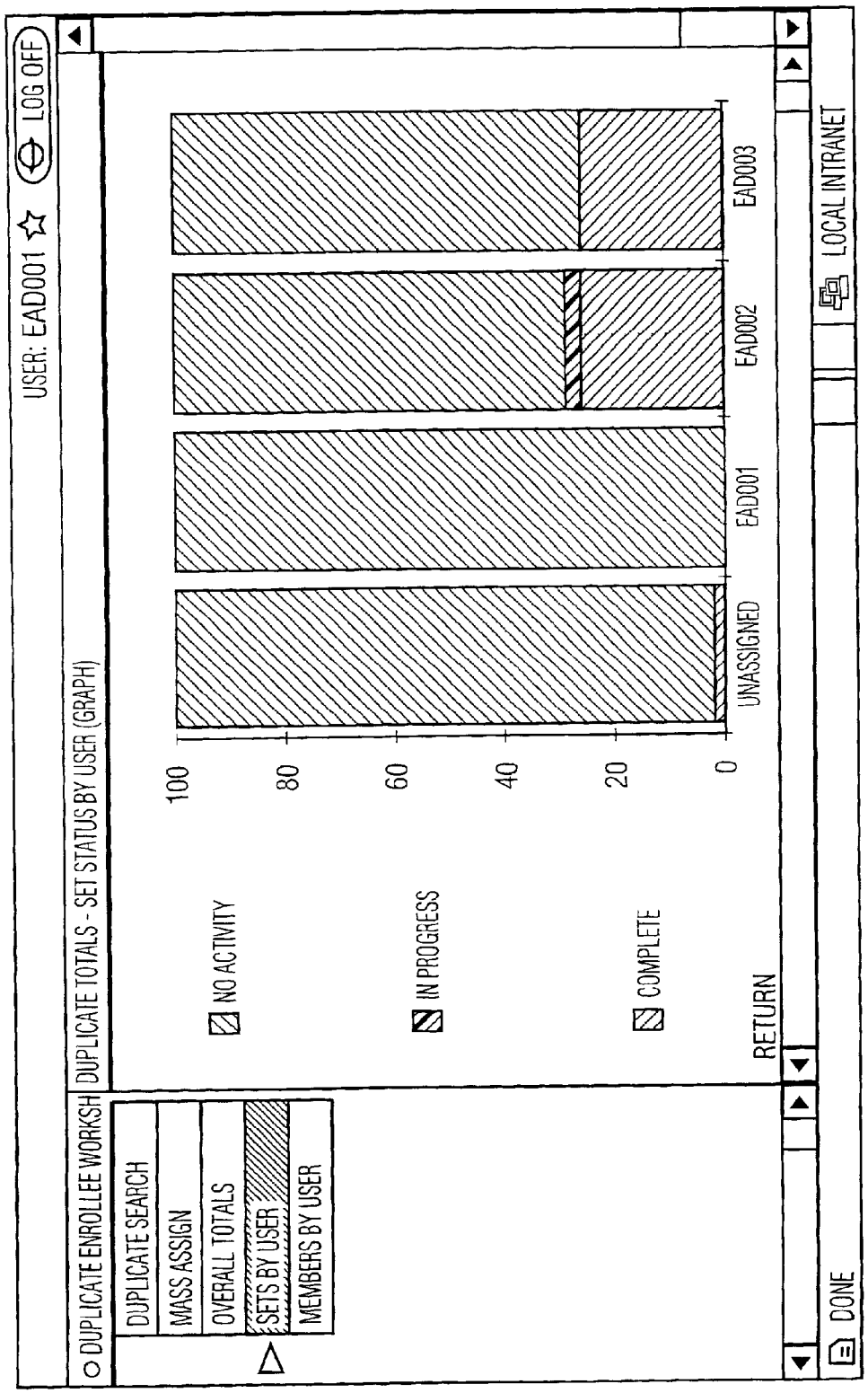
Figure 20:
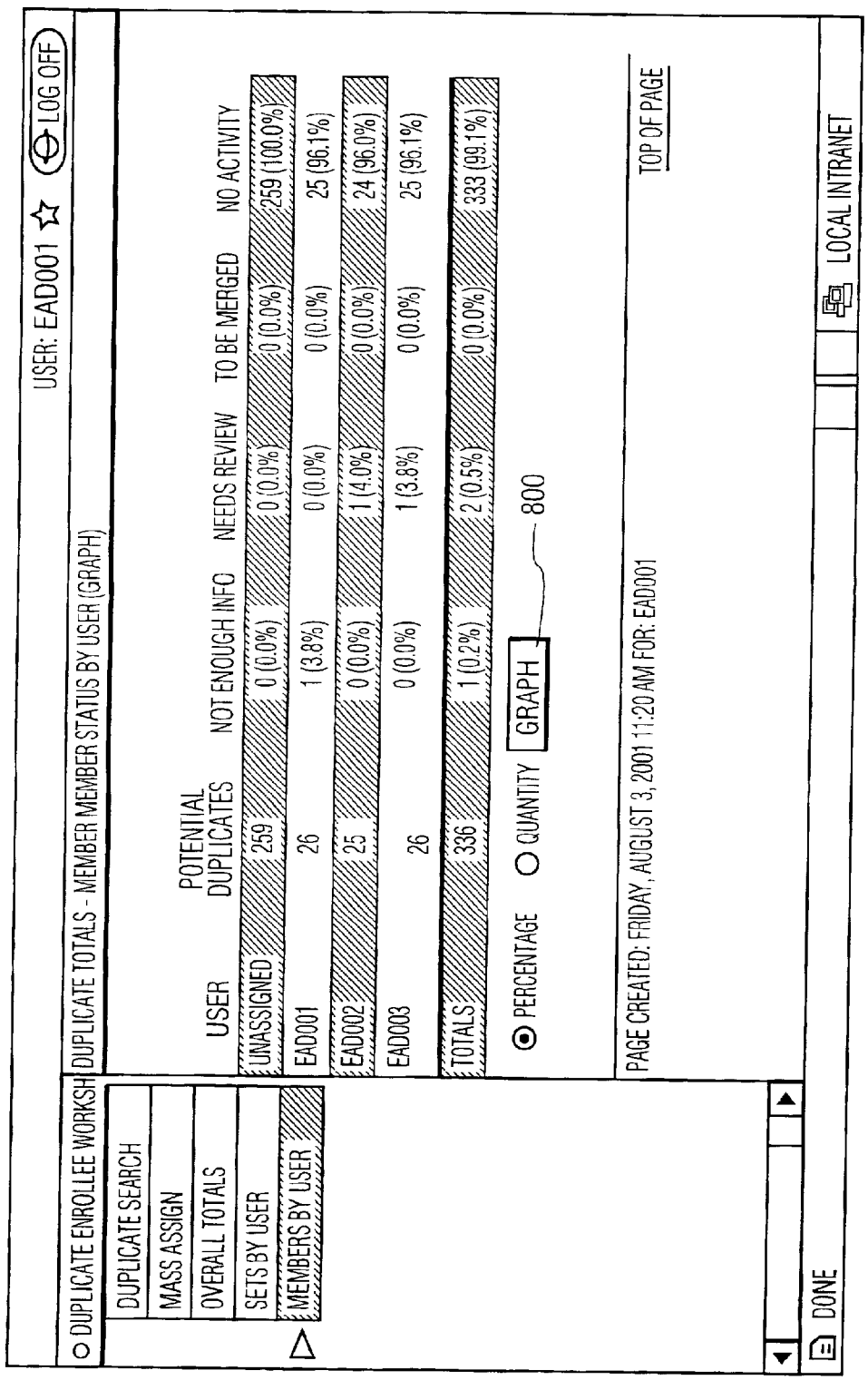
Figure 21:
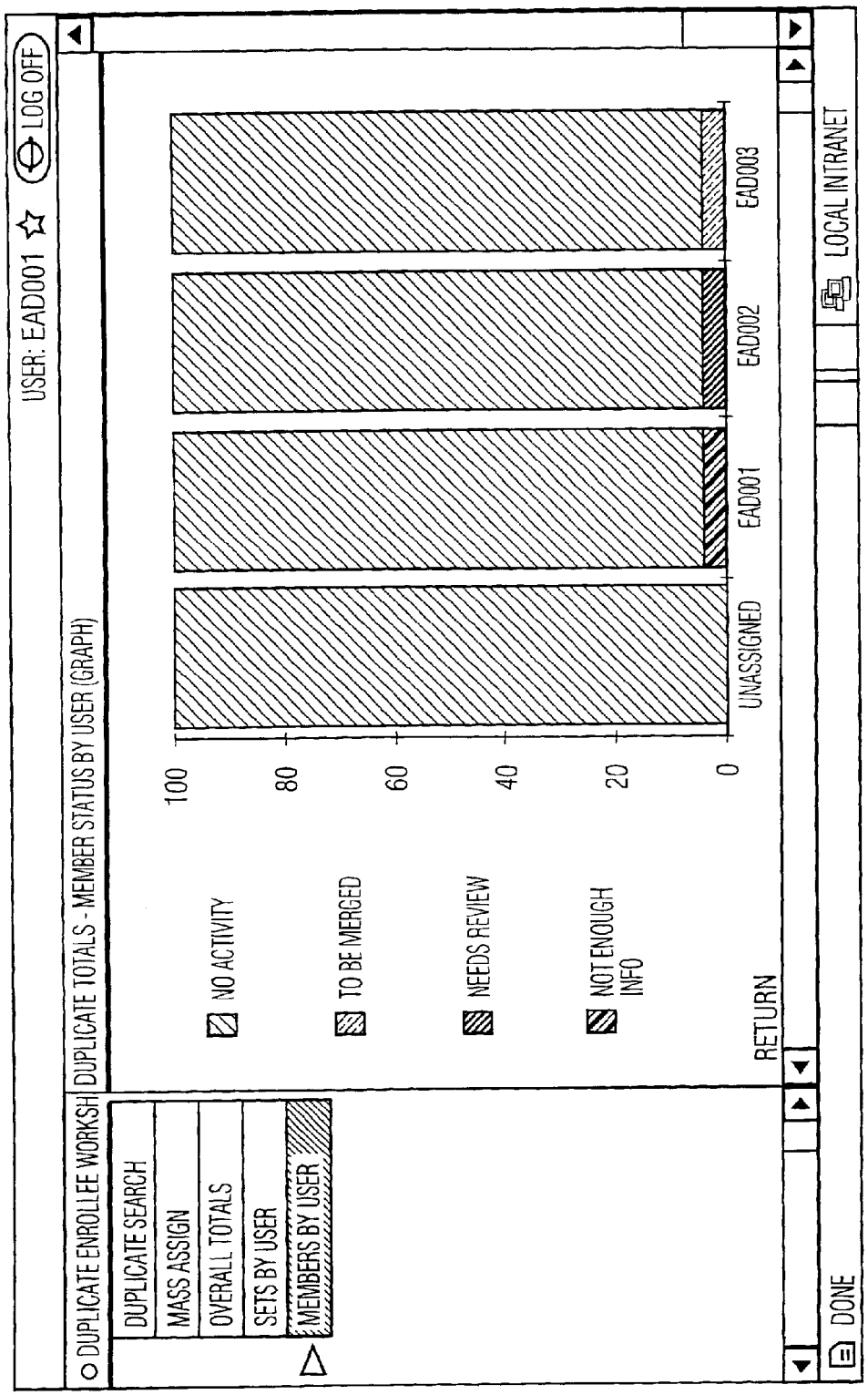

In step 489 of FIG. 4 a user interface window shown in FIG. 18 is generated in response to administrator command revealing the status of the assigned duplicate record sets by user. Further, the statistics given in FIG. 18 are presented in graphical form in FIG. 19, in response to user selection of graph icon 797 of FIG. 18. Similarly, in step 491 of FIG. 4, a user interface window shown in FIG. 20 is generated in response to administrator command revealing detailed status of duplicate records apportioned by user. In addition, the statistics given in FIG. 20 are presented in graphical form in FIG. 21, in response to user selection of graph icon 800 of FIG. 20. The data of FIG. 20 (and also FIG. 18) may also be selected for display by a user either as percentage or quantity data.

The systems and processes presented in FIGS. 1–4 as well as the user interface display images presented in FIGS. 5–21 are not exclusive. Other systems, processes and user interface images may be derived in accordance with the principles of the invention to accomplish the same objectives. The inventive principles may be applied in a variety of environments for identifying and consolidating duplicate records as well as for resolving duplicate records and managing the associated workload and for automatically continuously improving system operation based on analysis of results. Specifically, the inventive principles are applicable to identify and consolidate duplicate records or files derived from any record repository or combination of repositories involving any types of data, not just healthcare data, wherever duplicate records pose a burden.

What is claimed is:

1. A method for consolidating multiple records associated with a single entity and stored in at least one record repository, comprising the steps of:

identifying a first record;

identifying a second record;

applying record matching criteria to compare data element content of said first and second identified records to determine commonality data indicative of a likelihood said first and second records are associated with a common entity; and merging said first and second record content into a composite record in response to said determined commonality data and excluding at least a portion of replicated and redundant information occurring in said content.

2. A method according to claim 1, including the step of, selecting one of said first and second records as a surviving record based on at least one of, (a) earliest date of record creation and (b) relative content of said first and second records and transferring a first identified element of the non-selected record into said surviving record to form said composite record.

3. A method according to claim 2, including the step of, substituting identified elements of the selected record for corresponding elements of the non-selected record for inclusion in said composite record.

4. A method according to claim 1, including the step of, initiating generation of a record comparison menu showing a first data item of said first record and a corresponding second data item of said second record and prompting a user to select one of said first and second data items for inclusion in said composite record.

5. A method according to claim 4, wherein said record comparison menu shows said first data item of said first record and said corresponding second data item of said second record side by side for comparison.

6. A method according to claim 1, including the step of, initiating generation of a record comparison menu showing a first data item of said first record and a corresponding second data item of said second record in response to detection of at least one of, (a) a particular data element in either of said first or said second record and (b) a difference in data content of a record field common to said first and second records.

7. A method according to claim 1, wherein said steps of identifying first and second records comprise identifying said first and second records using first and second record identifiers respectively.

8. A method according to claim 1, wherein said step of applying said record matching criteria comprises parsing said first and second records to identify presence of a plurality of predetermined record fields using probabilistic matching for particular text items.

9. A method according to claim 1, wherein said commonality data comprises a measure quantifying detected occurrence of predetermined record items in both said first and said second records.

10. A method according to claim 9, wherein said predetermined record items comprise at least one of, (a) text strings and (b) record fields identified by keyword text items.

11. A method according to claim 1, wherein said merging step includes merging clinical data comprising at least one of (a) electro-cardiograph (ECG) or electro-encepholograph (EEG) data, (b) x-ray data, (c) laboratory test result data, (d) physical characteristic data, (e) previous diagnosis data, (f) allergy data, (g) ventilation data, (h) blood oxygen or pressure data, (i) infusion pump data and (j) pulse data.

12. A method according to claim 1, wherein said entity comprises at least one of, (a) a patient, (b) an individual, (c) a company, (d) an organization, and (e) a goods item.

13. A method according to claim 1, including the step of, at least one of, (a) deleting a redundant identifier identifying an item common to both said first and second record from said composite record, and (b) amending an identifier identifying an item common to both said first and second record in said composite record.

14. A method for consolidating multiple healthcare records associated with a patient and stored in at least one record repository, comprising the steps of:

in response to a single entry of user identification and password information for accessing a plurality of concurrently operating applications for, identifying a first record;

identifying a second record;

applying record matching criteria to compare data element content of said first and second identified records to determine commonality data indicative of a likelihood said first and second records are associated with a common patient; and merging said first and second record content into a composite record in response to said determined commonality data and excluding at least a portion of replicated and redundant information occurring in said content.

15. A method according to claim 14, including the step of, at least one of, (a) deleting a redundant identifier identifying an item common to both said first and second record from said composite record, and (b) amending an identifier identifying an item common to both said first and second record in said composite record.

16. A method according to claim 15, wherein
said redundant identifier identifying an item common to both said first and second record comprises an identifier identifying at least one of, (a) a specific patient, (b) a patient record, (c) an element of a patient record and (d) particular patient clinical data.

17. A method according to claim 14, including the step of,
selecting one of said first and second records as a surviving record based on at least one of, (a) earliest date of record creation and (b) relative content of said first and second records and
automatically transferring a first identified element of the non-selected record into said surviving record to form said composite record.

18. A method according to claim 17, wherein
said transferred first identified element comprises at least one of, (a) a user identifier, and (b) record entries concerning medical services delivered to said patient.

19. A method according to claim 17, including the step of,
automatically substituting identified non-clinical elements of the selected record for corresponding elements of the non-selected record for inclusion in said composite record.

20. A method according to claim 19, wherein
said substituted identified elements comprise at least one of, (a) patient address information, (b) patient name, (c) patient physical characteristics and (d) patient non-clinical data.

21. A method according to claim 19, including the step of,
applying a substitution rule for automatically substituting a particular element of said identified elements, said rule comprising at least one of, (a) include only said particular element of said first record in said composite record, (b) include only said particular element of said second record in said composite record, (c) include only a first record particular element, if present in said first record, in said composite record, and (d) include only a second record particular element, if present in said second record, in said composite record.

22. A method according to claim 21, including the step of,
wherein different substitution rules are applicable to particular data items of said first and second records in response to user selection.

23. A method according to claim 14, wherein
said merging step comprises the step of incorporating clinical data of both said first and second records in said composite record.

24. A method according to claim 23, wherein
said step of merging clinical data comprises automatically merging clinical data of said first and second records unless a predetermined condition is satisfied indicating said clinical data is to be merged subject to manual involvement.

25. A method according to claim 14, including the step of,
applying different rules in merging clinical data than in merging non-clinical data of said first and second records.

26. A method for consolidating multiple records associated with a single entity and stored in at least one record repository, comprising the steps of:
identifying first and second records as being associated with a single entity;
determining from stored record information whether said first and second records are indicated as being associated with different entities;
in response to said determination, applying record matching criteria to compare data element content of said first and second identified records to determine commonality data indicative of a likelihood said first and second records are associated with a common entity; and
merging said first and second record content into a composite record in response to said determined commonality data by excluding at least a portion of replicated and redundant information occurring in said content.

27. A method according to claim 26, including the step of,
receiving and storing an indication said first and second records are associated with different entities in response to a previous determination said first and second records were falsely identified as being associated with a single entity.

28. A method according to claim 24, wherein
said predetermined condition identifies at least one of, (a) said patient is on a physician patient list and (b) said clinical data of said second record duplicates said clinical data of said first record.

* * * * *